United States Patent [19]

Babb

[11] Patent Number: 4,528,178
[45] Date of Patent: Jul. 9, 1985

[54] CHEMOTHERAPEUTIC AGENT AND TRACER COMPOSITION AND USE THEREOF

[75] Inventor: Albert L. Babb, Seattle, Wash.

[73] Assignee: Biomedics, Inc., Santa Ana, Calif.

[21] Appl. No.: 377,383

[22] Filed: May 12, 1982

Related U.S. Application Data

[62] Division of Ser. No. 48,334, Jun. 14, 1979, Pat. No. 4,329,986.

[51] Int. Cl.³ .................. G01N 33/48; G01N 31/00; A61K 33/00
[52] U.S. Cl. .................. 424/7.1; 424/129; 436/63; 436/172; 436/800; 436/805; 436/811; 436/815; 128/653; 128/659; 128/760; 210/645; 210/646; 210/647; 210/648; 210/651; 210/321.3; 210/927
[58] Field of Search ............... 424/7.1, 9, 129; 436/63, 172, 800, 811, 805, 815; 128/653, 659, 760; 210/645–648, 651, 321.3, 927

[56] References Cited

U.S. PATENT DOCUMENTS 4,017,614  4/1977  Wild .................... 424/324

OTHER PUBLICATIONS

Babb, Report Carbamylated Red Cell Distributions in Blood Treated Extracorporeally with Cyanate, Nat. Heart, Lung & Blood Inst., Bethesda MD, Contract NO1-HB-6-2962, Jul. 1977.

Primary Examiner—Robert J. Warden
Assistant Examiner—K. S. Moss

[57]  ABSTRACT

A therapeutic composition suitable for extracorporeal treatment of whole blood comprises a dialyzable chemotherapeutic agent and a dialyzable fluorescable tracer means. The removal rate of the fluorescable tracer compound from treated blood during hemodialysis is a function of the removal rate of unreacted chemotherapeutic agent present. The residual chemotherapeutic agent concentration after hemodialysis is ascertained by measuring the concentration of the fluorescable tracer compound in a dialysate using fluorometric techniques.

12 Claims, No Drawings

CHEMOTHERAPEUTIC AGENT AND TRACER COMPOSITION AND USE THEREOF

This is a division of application Ser. No. 48,334, filed June 14, 1979, now U.S. Pat. No. 4,329,986, issued May 18, 1982.

FIELD OF THE INVENTION

This invention relates to compositions suitable for the extracorporeal treatment of whole blood. One aspect of this invention relates to compositions for the treatment of sickle cell anemia.

BACKGROUND OF THE INVENTION

Sickle cell anemia, the world's most common molecular disease, is the result of a single amino acid substitution at a surface position on the beta chain of hemoglobin. The only difference in primary chemical structure between normal hemoglobin (HbA) and sickle cell hemoglobin (HbS) is the substitution of valine for glutamic acid at the sixth amino acid from the NH$_2$-terminal of the beta chain.

The treatment of sickle cell anemia by inhibition of sickling using techniques of protein engineering is known. In particular, it is known that cyanate is useful to prevent the sickling of red blood cells of sickle cell anemia patients. See, for example, U.S. Pat. No. 3,833,724 to Cerami et al. It is also known that isocyanic acid, the reactive form of cyanate will react irreversibly with free amino groups of hemoglobin, primarily at the terminal valine position to decrease the polymerization of deoxyhemoglobin S molecules.

In HbS, the resulting carbamylation of the amino termini of the $\alpha$- and $\beta$-chains that are present produces definite functional alterations such as an increase in oxygen affinity and a reduction in the Bohr effect. It is believed that carbamylation of the amino termini removes some of the salt bridges that stabilize the deoxy configuration of the hemoglobin tetramer present. Thus, carbamylation of HbS amino termini provides species of molecules which may not participate in the formation of tactoids. It has also been demonstrated that carbamylation of HbS prolongs considerably the survival of the red cells of the HbS homozygocytes without considerably affecting the red cell metabolism.

There are two major problem areas related to the use of cyanate in patients, however. The first problem area involves toxic effects due to non-specific carbamylation. Although the findings from animal experimentation appear rather optimistic, it is known that cyanate is a very reactive chemical with no specific affinity for hemoglobin. Intravenous or intraperitoneal administration of cyanate in mice has been shown to produce carbamylation of several enzymes in tissues other than blood, including the brain. Similar effects have been observed in *Macacca Nemestrina* after chronic administration of cyanate. Although the functional significance of this non-specific carbamylation remains to be assessed, such findings point to the need for maximum care, particularly in the chronic intravenous use of this drug.

The second problem area involves achieving effective levels of hemoglobin modification in vivo. From the available in vitro evidence, it appears that protection from sickling requires the carbamylation of at least one amino terminal valine per HbS tetramer. Such levels of carbamylation are not easily achieved with oral administration of non-toxic doses of cyanate; the reported carbamylation levels in homozygous sicklers treated with cyanate by mouth have been about 0.3 carbamyl groups per tetramer. This low degree of carbamylation may explain the relatively unimpressive effects in patients routinely treated with cyanate orally. An effective degree of carbamylation with intravenous administration of cyanate in an attempt to affect a sickling crisis is out of the question because toxic doses of the drug may be reached before one achieves the desired therapeutic effects. On the other hand, the intravenous administration of 5 to 10 gm of cyanate (LD$_{50}$=250 mg/kg) to sickle cell anemia patients, has resulted in only 0.4 to 0.6 carbamyl groups per tetramer.

To overcome the foregoing problems, extracorporeal treatment of whole blood with cyanate has been suggested, followed by removal of unreacted cyanate from the treated blood by hemodialysis before the blood is returned to the patient. In this manner, efficient carbamylation of HbS can be effected within a relatively short time period. However, in view of the recognized toxicity of cyanate, it is necessary to have a rapid, effective means for detecting the cyanate concentration in blood after hemodialysis so that the efficacy of cyanate removal during the hemodialysis step can be monitored and also so that free cyanate in the blood returned to the patient does not exceed a physiologically tolerable level.

To this end, it has been proposed to introduce cyanate into the blood to be treated as potassium cyanate (KNCO) and to monitor the cyanate concentration in whole blood by a pair of K$^+$-sensitive electrodes that compare the concentration of K$^+$ in blood before and after the treatment, Kjellstrand et al., *Trans. Amer. Soc. Artif. Int. Organs*, vol. XX, 574–577 (1974). However, the foregoing approach is not satisfactory because the measurement of K$^+$ concentration in whole blood does not give a reliable indication of the cyanate concentration that may be present because relatively large stores of potassium are already present in the patient's body.

Accordingly, there exists a pressing need for a safe and reliable means for determining the concentration of the cyanate content of whole blood before a practical treatment can be provided to patients suffering from sickle cell anemia. The present invention satisfies this need.

SUMMARY OF THE INVENTION

The present invention contemplates the introduction of a fluorescable tracer compound into blood that is to be subjected to an extracorporeal treatment with a chemotherapeutic agent. The fluorescable tracer compound is water-soluble, dialyzable, physiologically tolerable, substantially inert with respect to blood proteins, and compatible with the chemotherapeutic agent employed. The removal rate of fluorescable tracer compound from the treated blood during hemodialysis is a function of the removal rate of unreacted chemotherapeutic agent present, thus the amount of chemotherapeutic agent remaining in the blood after hemodialysis is ascertained by measuring the amount of fluorescable tracer compound present in the obtained dialysate.

Concentration of a dialyzable chemotherapeutic agent in an extracorporeal stream of whole blood containing the chemotherapeutic agent and the fluorescable tracer compound is measured by first contacting at least a portion of the extracorporeal stream across a dialysis membrane with an aqueous dialysis solution that is devoid of the tracer compound for a predetermined time period, thereafter recovering the dialysis solution and irradiating an aliquot thereof with fluorescence exciting electromagnetic radiation, and measuring the intensity of the emitted fluorescence. The latter operation can be performed by passing the irradiated aliquot over a detector, such as a photomultiplier tube, responsive to the fluorescence emitted by the tracer compound present in the irradiated aliquot and generating an electrical signal having a magnitude indicative of the intensity of the emitted fluorescence, and then energizing an indicator with the signal generated by the detector. Preferably the aforementioned time period is of sufficient duration to substantially equilibrate the concentration of the tracer compound in the extracorporeal blood stream with that in the dialysis solution.

A particularly preferred therapeutic composition, suitable for extracorporeal treatment of whole blood, comprises a water-soluble cyanate and salicylamide in a weight ratio of about 20:1 to about 50:1, respectively, and more preferably at a weight ratio of about 35:1, respectively. In chemotherapy of sickle cell anemia by extracorporeal treatment of blood withdrawn from the patient and subsequently returned, the foregoing composition is used as an aqueous solution in which cyanate is present in a concentration of about 0.20 molar to about 0.60 molar and the salicylamide is present in a concentration of about 2.5 millimolar to about 8.5 millimolar. Preferably the cyanate concentration in the blood stream undergoing treatment is about 0.02 molar.

To ascertain the amount of cyanate present in blood after hemodialysis the amount of salicylamide in dialysate is ascertained. To this end, an aliquot of dialysate is irradiated with fluorescence-exciting electromagnetic radiation and the intensity of fluorescence emitted by salicylamide is measured. The intensity of emitted fluorescence is a function of salicylamide concentration in the aliquot, and thus an indication of the cyanate concentration.

DESCRIPTION OF PREFERRED EMBODIMENTS

Preferred fluorescable tracer compounds suitable for the purposes of the present invention are N-monosubstituted benzamides represented by the formula

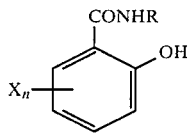

wherein R can be hydrogen or methyl, X can be a halogen, such as fluorine, chlorine, bromine or iodine, or alkoxy having no more than two carbon atoms, e.g., methoxy and ethoxy, and n is an integer having a value of 0 or 1. Physiologically tolerable alkali metal salts of the foregoing compounds, e.g., the sodium salts, are also suitable.

Salicylamide is a particularly preferred tracer compound. Salicylamide (M.W. about 137.12), also known as o-hydroxybenzamide, is commercially available and is frequently utilized as a constituent of pain remedies. Salicylamide has no known tendency to bind to blood proteins or to interfere with platelet aggregation. When introduced into a mammalian blood stream intracorporeally, it is present in the plasma fraction predominantly in the conjugated form. The plasma levels of salicylamide remain extremly low, presumably due to accumulation in tissues and rapid excretion via the kidneys.

Upon excitation by ultraviolet radiation having a wavelength of about 318 nanometers, salicylamide fluoresces with a blue light having a wavelength about 410 nanometers. The intensity of fluorescence is dependent on concentration, pH and temperature, thus for the monitoring of concentration changes in a given salicylamide-containing solution, the pH and temperature should be controlled. Preferably, the pH value of the salicylamide-containing solution is maintained in a range within ±0.05 and the temperature is maintained within a range of about ±0.5° C. To this end it is desirable to use a buffered solution the temperature of which is controlled within the desired limits. A suitable buffer for this purpose is the monobasic potassium phosphate buffer (pH=7.4) or the like. Such buffers are commerically available.

As used herein and in the appended claims, the term "cyanate" is intended to mean a compound providing or containing a reactive cyanate (—NCO) group. For carbamylation of HbS one such suitable compound is isocyanic acid (HNCO) either in its ionized or unionized form. A suitable source of isocyanic acid, in turn, can be sodium cyanate (NaNCO) which is in equilibrium with isocyanic acid when in an aqueous medium, i.e.:

$NaNCO + H_2O \rightleftharpoons HNCO + Na^+ + OH^-$

Other alkali metal cyanates, e.g., potassium cyanate, can also be used. In general, any water-soluble physiologically tolerable cyanate salt can be used. Also suitable as cyanate sources are the dialyzable alkyl ureas of which the $C_1$ to $C_4$ alkyl ureas, e.g., N,N'-dimethylurea, N,N-diethylurea, N-methyl-N'-butyl urea, N,N'-dipropylurea, N-ethylurea, N-butylurea and the like are preferred.

Other suitable chemotherapeutic agents that can be used in conjunction with a fluorescable tracer compound for the extracorporeal treatment of the blood of sickle cell anemia patients are the nitrogen mustards, the alkyl acetimidates, e.g., methylacetimidate or the like, the dialkyl adipimates, e.g. dimethyl adipimate, or the like.

In the case of carbamylation by a cyanate, the therapeutic compositions of the present invention can be compounded in dry form. A preferred therapeutic composition has a cyanate-to-salicylamide weight ratio of about 20:1 to about 50:1, respectively, and preferably a respective weight ratio of about 35:1. Alternatively, the present compositions can be aqueous solutions containing the foregoing ingredients. The cyanate can be present in a concentration of about 0.2 molar to about 0.6 molar, and salicylamide can be present in a concentration of about 2.5 millimolar to about 8.5 millimolar. A cyanate-to-salicylamide molar ratio of about 75 is preferred.

If desired, buffering agents and anticoagulants such as heparin may also be present.

A typical composition embodying the present invention is compounded as follows:
  sodium cyanate: 27.3 grams
  salicylamide: 0.77 grams
  sterile water, q.s. to 1000 milliliters
The pH of the resulting aqueous solution is then adjusted to a desired alkalinity, usually to a pH of about 8 or higher, using a physiologically tolerable alkaline compound, e.g., NaOH or a buffer, the solution is filtered e.g., through a 0.22-micron Millipore filter, and thereafter packaged in conventional intravenous containers. The solution can also be prepared using an isotonic (pH 7.4) buffer solution such as Normosol-R[1], commercially available from Abbott Laboratories, North Chicago, Ill.

[1] Per 100 milliliters of aqueous solution Normosol-R contains the following dissolved ingredients:

| NaCl | 526 mg | Na | 140 meq/l |
|---|---|---|---|
| Na acetate | 222 mg | K | 5 meq/l |
| Na gluconate | 502 mg | Mg | 3 meq/l |
| KCl | 37 mg | Cl | 98 meq/l |
| MgCl$_2$ | 14 mg | Acetate | 27 meq/l |
| | | Gluconate | 23 meq/l |

For chemotherapy of a patient afflicted with sickle cell anemia, the foregoing aqueous solution is infused into an extracorporeal blood stream of the patient passing through a suitable hemoreactor, e.g., a cartridge comprising a coil or a plurality of hollow tubes, at a volumetric flow rate ratio of about 30:1 to about 10:1, that is, at a blood flow rate of about 30 to about 10 milliliters per minute the cyanate- and salicylamide-containing aqueous solution is infused at a rate of about one milliliter per minute. A preferred residence time of the blood within the hemoreactor is about ten minutes.

For carbamylation of HbS, the concentration of cyanate in the patient's extracorporeal blood stream can be in the range of about 0.01 molar to about 0.03 molar, and preferably is about 0.02 molar. Usually about 10 weight percent of the cyanate present reacts with HbS during the treatment. The salicylamide concentration in the extracorporeal blood stream during the foregoing carbamylation treatment can be about 0.14 millimolar to about 0.4 millimolar, and preferably is about 0.27 millimolar.

Thereafter unreacted cyanate together with salicylamide are removed from the treated blood stream in a hemodialyzer using a conventional dialysate. A typical dialysate suitable for this purpose has the following composition[1]:

[1] For use with trisodium citrate as anticoagulant; since the dialysate contains no calcium, Ca$^{++}$ is subsequently added as heparinized aqueous CaCl$_2$ solution before the treated and dialyzed blood is returned to the patient. If heparin is the only anticoagulant used, then calcium ion can be present in the dialysate.

| sodium ion | 135 meq/liter |
|---|---|
| chloride ion | 101 |
| magnesium ion | 1 |
| acetate ion | 38 |

After dialysis of the extracorporeal blood stream has been effected, the concentration of salicylamide, and thus cyanate, in this blood stream is ascertained by subjecting the dialysate to fluorometric analysis either directly or after a dilution, as desired for optimum determination of concentration. Alternatively, the blood stream, or a portion thereof, can be passed through a hemo-analyzer which in effect is a secondary dialyzer in which an aqueous alkaline solution, e.g., an isotonic saline solution or a Normosol-R solution having a predetermined alkaline pH, at a predetermined temperature, passes countercurrent to the blood stream as a secondary dialysate solution devoid of salicylamide. A conventional dialysis membrane, e.g., of the type shown in U.S. Pat. No. 4,031,012 to Gics, or the like, separates the secondary dialysate solution from the blood stream. The residence time of the respective countercurrent streams within the hemoanalyzer preferably is selected so that equilibration of the salicylamide concentration in both streams across the dialysis membrane is substantially achieved. Thereafter the obtained dialysate is subjected to fluorometric analytical techniques so as to measure intensity of fluorescence and thus the salicylamide concentration therein, e.g., by using a commercially available fluorometer, such as a Turner Spectrofluorometer or the like. Fluorescable tracer means other than salicylamide can be handled in a similar manner.

During fluorometric analysis, the dialysate preferably is maintained at a pH and temperature that optimizes fluorescence. For salicylamide a pH of about 7.4 and a temperature of about 41° C. are preferred. However, the pH value can vary within the range of about 7.35 to about 7.45 and the temperature within the range of about 39.5° C. to about 41.5° C. In any event, during fluorometry the aqueous dialysate solution containing the fluorescable tracer compound, e.g., salicylamide, should be maintained as closely as possible at the same pH and temperature as was used for calibration of the fluorometer since fluorometry is quite sensitive to both pH and temperature.

The relative flow rates of the blood stream and the secondary dialysate in any given instance will depend, of course, on the type of hemo-analyzer used, the characteristics of the semipermeable membranes that separate the two streams, and similar factors. In a typical instance, a dialysate flow rate of about 0.2 milliliters per minute through the tube side of a shell-and-tube hemoanalyzer comprising hollow, semi-permeable fibers as the tubes and a blood flow rate of about 40 milliliters per minute or less through the shell side of the hemoanalyzer will permit a degree of equilibration of nearly 100 percent.

The present invention is further illustrated by the following example.

EXAMPLE 1

Determination of Cyanate Content in Blood Stream

Whole blood is contacted in a hemo-reactor with an aqueous solution of sodium cyanate (about 0.42 molar) and salicylamide (about 5.6 millimolar) at a flow rate sufficient to maintain a blood stream HNCO concentration of about 20 millimolar during the treatment and is then detoxified in a Travenol CF 1500 hollow fiber dialyzer having an effective dialysis area of about 1.5 square meters. The dialysate composition is as follows:

| sodium ion | 135 meq/liter |
|---|---|
| chloride ion | 101 meq/liter |
| magnesium ion | 1 meq/liter |
| acetate ion | 38 meq/liter |

The blood flow rate through the dialyzer is about 40 milliliters/minute.

The concentration of salicylamide in the blood stream leaving the dialyzer is determined by subjecting this blood stream to a secondary dialysis with Normosol-R at 37° C. and pH 7.4. The obtained secondary dialysate is then subjected to fluorometric analysis by irradiating with UV radiation having a wavelength of about 318 nanometers and measuring the intensity of fluorescence at about 410 nanometers using a photomultiplier tube (RCA 4552) and optical filters (Schott KV-418, BG-12 and UG-1). Utilizing the known ratio of cyanate to salicylamide in the infusate, the dialysis rates for cyanate and salicylamide, and a calibration curve of fluorescence intensity versus salicylamide concentration, the following information is obtained:

| Cyanate Removal Efficiency in Dialyzer Percent | Fluorescence Intensity, Millivolts | Cyanate Concentration, Millimolar |
|---|---|---|
| 99 | 100 | 0.21 ± 0.01 |
| 98 | 122 | 0.40 ± 0.02 |
| 97 | 167 | 0.60 ± 0.03 |
| 96 | 239 | 1.0 ± 0.05 |
| 95 | 389 | 2.0 ± 0.10 |

While in the foregoing example salicylamide is the fluorescent tracer compound that is utilized in conjunction with a cyanate as the dialyzable, water-soluble therapeutic agent, other fluorescable tracer compounds that do not bind to plasma proteins can be used as well. The fluorescable tracer compounds, of course, have to be water-soluble, and dialyzable, and the extraction efficiency during dialysis preferably should approximate that of the chemotherapeutic agent. Preferably the water solubility of the fluorescable tracer compound at 37° C. is at least about 1.0 grams/liter. For use in the treatment of sickle cell anemia by carbamylation, the fluorescable tracer compound preferably should fluoresce at about 40° C.±0.1° and at a pH of about 7.4±0.05.

To determine the concentration of a dialyzable chemotherapeutic agent in a blood stream after dialysis, the present invention contemplates introducing a fluorescable tracer means into a patient's whole blood stream together with the chemotherapeutic agent, thereafter subjecting the whole blood to dialysis so as to remove therefrom the chemotherapeutic agent and the tracer means at rates that are a function of one another. The obtained dialysate can then be subjected to conventional fluorometric analysis.

While in some cases a portion of the dialysate can be analyzed fluorometrically without more, in view of the relatively high concentration of salicylamide, or similar fluorescable tracer compound in the dialysate that may be present, usually it is desirable to dilute the dialysate portion that is to be subjected to fluorometric analysis in order to enhance accuracy of the measurement. From the flow rates of the respective fluids introducing the tracer compound into the system and removing the tracer compound from the system, and from the degree of dialysate dilution, if any, during fluorometric analysis the residual amount of the tracer compound, if any, that remains in the blood stream returned to the patient after extracorporeal treatment can be calculated using conventional material balance procedures. An appropriately programmed microprocessor is particularly well suited for this purpose. Once the concentration of the tracer compound in the blood stream being returned to the patient is determined, the maximum possible concentration of cyanate in that blood stream is ascertained. Inasmuch as at least some of the cyanate initially introduced into the blood stream will have reacted with HbS, the actual cyanate concentration in the returned blood stream will, of course, be less than the ascertained maximum and the fluormetric determination of concentration will be conservative.

Alternatively, the concentration of the chemotherapeutic agent remaining in the blood stream after hemodialysis can be ascertained by removing the tracer compound remaining in the dialyzed whole blood, if any is present, during a secondary dialysis step in the form of an aqueous dialysate or extract. The concentration of the tracer compound in this extract also is a known function of the concentration of the tracer means in the dialyzed whole blood and thus also proportional to the residual concentration of the chemotherapeutic agent in the dialyzed whole blood. Preferably, the secondary dialysate is substantially equilibrated with the dialyzed whole blood so that the concentration of the tracer compound, such as salicylamide, in the secondary dialysate is equal to or closely approximates the concentration of the tracer compound in the blood stream being returned to the patient.

In either case a dialysate portion is then irradiated with fluorescence-exciting electromagnetic radiation, and the intensity of the emitted fluorescence is ascertained by generating, by means of an appropriate detector such as a photomultiplier tube and associated circuitry, an electrical signal having a magnitude that is indicative of the intensity of the emitted fluorescence. The electrical signal, in turn, is used to energize an indicator means such as a meter, a warning light or buzzer, a recorder pen, or the like.

The foregoing specification is intended as illustrative and is not to be taken as limiting. Still other variations within the spirit and scope of this invention are possible and will readily present themselves to those skilled in the art.

I claim:

1. A therapeutic and detecting composition suitable for extracorporeal treatment of whole blood comprising a water-soluble chemotherapeutic agent for sickle cell anemia said agent being selected from the group consisting of a water-soluble cyanate containing a reactive —NCO group, an alkyl acetimidate, and an alkyl adipimate, and a water-soluble fluorescable tracer means, said tracer being selected from the group consisting of an N-substituted benzamide represented by the formula

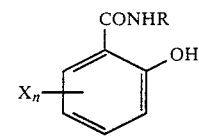

wherein R is a member of the group consisting of hydrogen and methyl, X is a member of the group consisting of halogen and alkoxy having no more than two carbon atoms, and n is an integer having a value of 0 or 1, and physiologically tolerable alkali metal salts thereof said chemotherapeutic agent and said tracer means being dialyzable from whole blood at rates that are a function of one another.

2. The therapeutic composition in accordance with claim 1 wherein the fluorescable tracer means is salicylamide.

3. The therapeutic composition in accordance with claim 1 wherein the chemotherapeutic agent is the water-soluble cyanate and the fluorescable tracer means is salicylamide.

4. A therapeutic and detecting composition suitable for extracorporeal treatment of whole blood and comprising a water-soluble cyanate containing a reactive —NCO group and salicylamide in a weight ratio of about 20:1 to about 50:1, respectively.

5. The therapeutic composition in accordance with claim 4 wherein the water-soluble cyanate is an alkali metal cyanate.

6. The therapeutic composition in accordance with claim 4 wherein the water-soluble cyanate is sodium cyanate and wherein the weight ratio of sodium cyanate to salicylamide is about 35:1.

7. The therapeutic and detecting composition suitable for extra-corporeal treatment of whole blood and comprising an aqueous solution containing cyanate containing a reactive —NCO group and salicylamide, the cyanate being present in a concentration of about 0.2 molar to about 0.6 molar and the salicylamide being present in a concentration of about 2.5 millimolar to about 8.5 millimolar.

8. The therapeutic composition in accordance with claim 7 wherein the cyanate concentration is about 0.42 molar and the salicylamide concentration is about 5.6 millimolar.

9. The therapeutic composition in accordance with claim 7 wherein the composition additionally contains a physiologically tolerable buffer maintaining the composition at a pH of about 7.4.

10. A method for determining the concentration of dialyzable chemotherapeutic agent for sickle cell anemia said agent being selected from the group consisting of a water-soluble cyanate containing a reactive —NCO group, an alkyl acetimidate, and an alkyl adipimate, in an extracorporeal stream of whole blood containing said chemotherapeutic agent and salicylamide which comprises the steps of:

contacting at least a portion of said extracorporeal stream across a dialysis membrane with an aqueous alkaline solution devoid of salicylamide for a predetermined time period;

thereafter recovering said aqueous alkaline solution;

irradiating an aliquot of the recovered aqueous alkaline solution with ultraviolet radiation haveing a wavelength of about 318 nanometers;

positioning the irradiated aliquot adjacent to a detector means generating an output signal in response to emitted radiation having a wavelength of about 410 nanometers, said signal being proportional to the intensity of the emitted radiation;

energizing the indicator means with said output signal and determining the concentration of remaining indicator wherein the concentration of remaining indicator is an indication of the concentration of the dialyzable chemotherapeutic agent present in the sample.

11. The method in accordance with claim 10 wherein the dialyzable chemotherapeutic agent is a water-soluble cyanate containing a reactive —NCO group.

12. The method in accordance with claim 10 wherein the dialyzable chemotherapeutic agent is isocyanic acid.

* * * * *